(12) United States Patent
Nakamura et al.

(10) Patent No.: US 12,097,099 B2
(45) Date of Patent: Sep. 24, 2024

(54) PRODUCTION METHOD OF ELASTIC COMPOSITE SHEET, ELASTIC COMPOSITE SHEET, AND DISPOSABLE WEARABLE ARTICLE USING SAID ELASTIC COMPOSITE SHEET

(71) Applicant: ZUIKO CORPORATION, Settu (JP)

(72) Inventors: Hideyuki Nakamura, Settu (JP); Yukihiko Fujita, Settu (JP); Ayako Kita, Settu (JP)

(73) Assignee: ZUIKO CORPORATION, Settu (JP)

( * ) Notice: Subject to any disclaimer, the term of this patent is extended or adjusted under 35 U.S.C. 154(b) by 1094 days.

(21) Appl. No.: 16/965,114

(22) PCT Filed: Dec. 17, 2018

(86) PCT No.: PCT/JP2018/046425
§ 371 (c)(1),
(2) Date: Jul. 27, 2020

(87) PCT Pub. No.: WO2019/150802
PCT Pub. Date: Aug. 8, 2019

(65) Prior Publication Data
US 2020/0360191 A1 Nov. 19, 2020

(30) Foreign Application Priority Data
Jan. 31, 2018 (JP) .................. 2018-014324

(51) Int. Cl.
*A61F 13/15* (2006.01)
*A61F 13/49* (2006.01)
(Continued)

(52) U.S. Cl.
CPC .. *A61F 13/15601* (2013.01); *A61F 13/15739* (2013.01); *A61F 13/15804* (2013.01);
(Continued)

(58) Field of Classification Search
CPC .......... A61F 13/15601; A61F 13/15739; A61F 13/15804; A61F 13/49019; A61F 13/4902;
(Continued)

(56) References Cited

U.S. PATENT DOCUMENTS

2003/0144643 A1   7/2003  Jarpenberg et al.
2004/0192140 A1   9/2004  Schneider et al.
(Continued)

FOREIGN PATENT DOCUMENTS

CN     1756659 A    4/2006
CN   101039804 A    9/2007
(Continued)

OTHER PUBLICATIONS

China National Intellectual Property Administration, "Office Action for Chinese Patent Application 201880088142.4," Oct. 8, 2021.
(Continued)

*Primary Examiner* — Daniel H Lee
(74) *Attorney, Agent, or Firm* — HAUPTMAN HAM, LLP

(57) ABSTRACT

In a production method of an elastic composite sheet, the elastic member does not break when the elastic member, in a stretched state, is bonded to a base material sheet; an elastic composite sheet and a disposable wearable article use the elastic composite sheet. A strip-shaped or string-shaped elastic member composed mainly of a thermoplastic elastic resin is stretched in the longitudinal direction of the elastic member. The stretched elastic member is placed over a first base material sheet such that the main surface of the first base material sheet contacts the elastic member. In this state, the elastic member and the first base material sheet are bonded in a first position that overlaps the elastic member seen from a direction perpendicular to the main surface of
(Continued)

the first base material sheet and that is away from the edges of the elastic member.

14 Claims, 7 Drawing Sheets

(51) Int. Cl.
    *B29C 65/00*      (2006.01)
    *B29C 65/08*      (2006.01)
    *B32B 5/02*      (2006.01)
    *B32B 7/05*      (2019.01)
    *B32B 25/10*      (2006.01)

(52) U.S. Cl.
    CPC .... *A61F 13/49019* (2013.01); *A61F 13/4902* (2013.01); *B29C 65/08* (2013.01); *B29C 66/21* (2013.01); *B29C 66/43* (2013.01); *B29C 66/7294* (2013.01); *B29C 66/7392* (2013.01); *B29C 66/84* (2013.01); *B32B 5/022* (2013.01); *B32B 7/05* (2019.01); *B32B 25/10* (2013.01); *B32B 2555/02* (2013.01)

(58) Field of Classification Search
    CPC ... A61F 13/15585; B29C 65/08; B29C 66/21; B29C 66/43; B29C 66/7294; B29C 66/7392; B29C 66/84; B29C 66/83411; B29C 66/83415; B29C 66/71; B29C 66/344; B29C 48/05; B29C 66/433; B29C 66/81433; B29C 66/83511; B29C 65/086; B32B 5/022; B32B 7/05; B32B 25/10; B32B 2555/02; B32B 37/04; B32B 37/0084; B32B 37/144; B29K 2995/0046; B29L 2031/4878
See application file for complete search history.

(56) References Cited

U.S. PATENT DOCUMENTS

| | | | |
|---|---|---|---|
| 2006/0009104 | A1 | 1/2006 | Schneider et al. |
| 2006/0083893 | A1 | 4/2006 | Ashraf |
| 2006/0270302 | A1 | 11/2006 | Ando et al. |
| 2007/0218245 | A1 | 9/2007 | Schneider et al. |
| 2009/0035527 | A1 | 2/2009 | Kobayashi et al. |
| 2010/0112313 | A1 | 5/2010 | Nakakado |
| 2010/0234823 | A1 | 9/2010 | Morita et al. |
| 2014/0073211 | A1 | 3/2014 | Bruce |
| 2014/0130956 | A1 | 5/2014 | Floberg et al. |
| 2016/0058624 | A1 | 3/2016 | Hohm et al. |
| 2018/0008481 | A1* | 1/2018 | Takahashi ............... B29C 66/21 |
| 2018/0014979 | A1 | 1/2018 | Fujita |
| 2018/0014984 | A1 | 1/2018 | Sakai |
| 2018/0015709 | A1* | 1/2018 | Takeuchi ............ B32B 37/0053 |
| 2018/0028371 | A1* | 2/2018 | Takaishi ............ A61F 13/49019 |
| 2018/0147094 | A1 | 5/2018 | Takeuchi |
| 2020/0383841 | A1 | 12/2020 | Sakai |
| 2020/0397623 | A1 | 12/2020 | Takahashi et al. |
| 2020/0397625 | A1 | 12/2020 | Sakai |
| 2020/0397626 | A1 | 12/2020 | Sakai |

FOREIGN PATENT DOCUMENTS

| | | |
|---|---|---|
| CN | 101166858 A | 4/2008 |
| CN | 101896336 A | 11/2010 |
| CN | 102834081 A | 12/2012 |
| CN | 104736754 A | 6/2015 |
| CN | 105358110 A | 2/2016 |
| CN | 107205856 A | 9/2017 |
| CN | 107205867 A | 9/2017 |
| CN | 107405228 A | 11/2017 |
| JP | 2005-080859 A | 3/2005 |
| JP | 2008-104853 A | 5/2008 |
| JP | 2014-520589 A | 8/2014 |
| JP | 2015-529165 A | 10/2015 |
| JP | 2016-140477 A | 8/2016 |
| WO | 2006/044813 A1 | 4/2006 |
| WO | 2008/126709 A1 | 10/2008 |
| WO | 2014/040048 A1 | 3/2014 |
| WO | 2014/208652 A1 | 12/2014 |
| WO | 2016/121986 A1 | 8/2016 |
| WO | 2016/181774 A1 | 11/2016 |

OTHER PUBLICATIONS

PCT/ISA/210, "International Search Report for International Application No. PCT/JP2018/046425," Mar. 12, 2019.

Europe Patent Office, "Search Report for European Patent Application No. 18904206.2," Oct. 29, 2021.

* cited by examiner

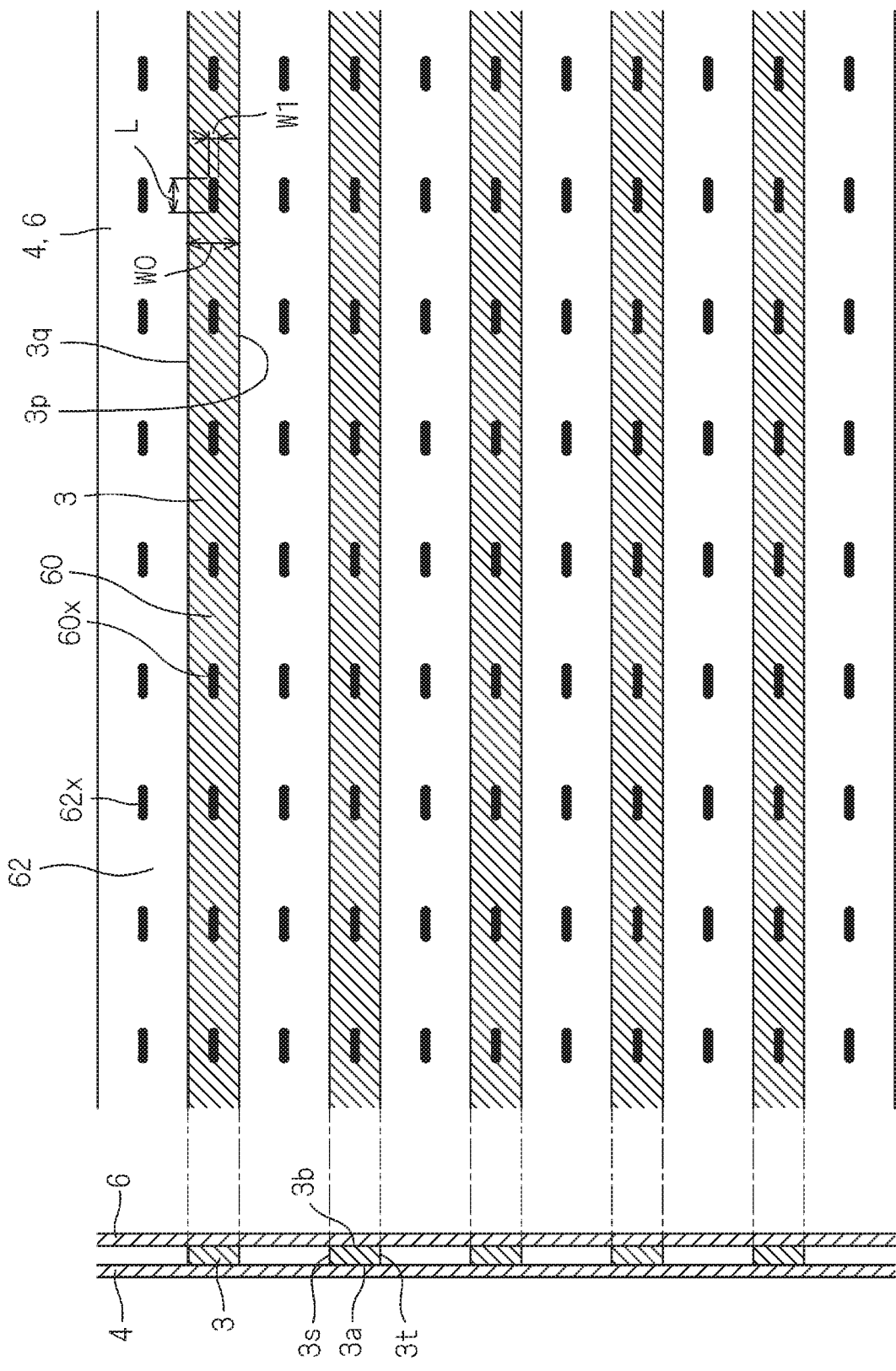

Fig. 9
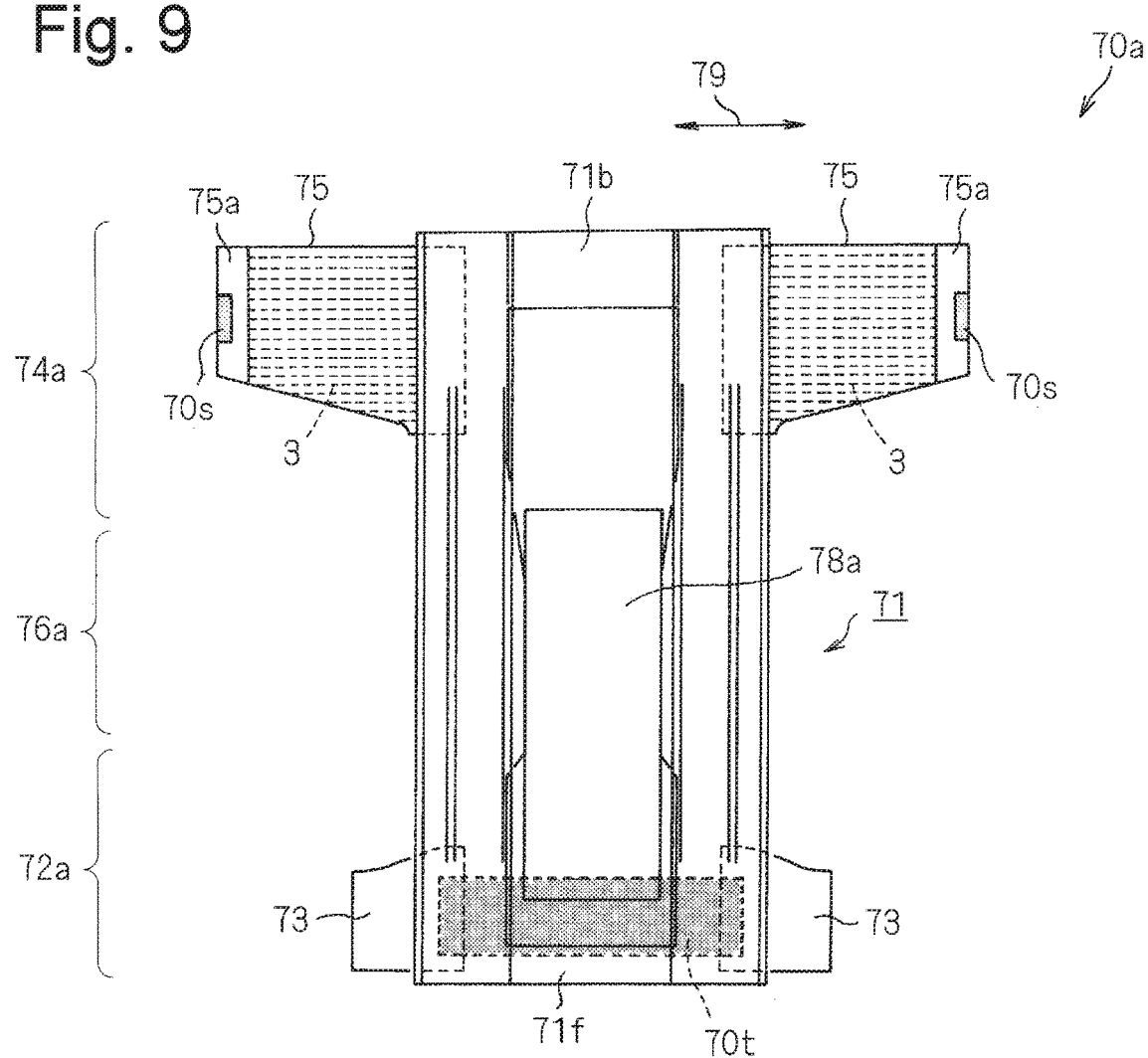
Fig. 10  --Prior Art--
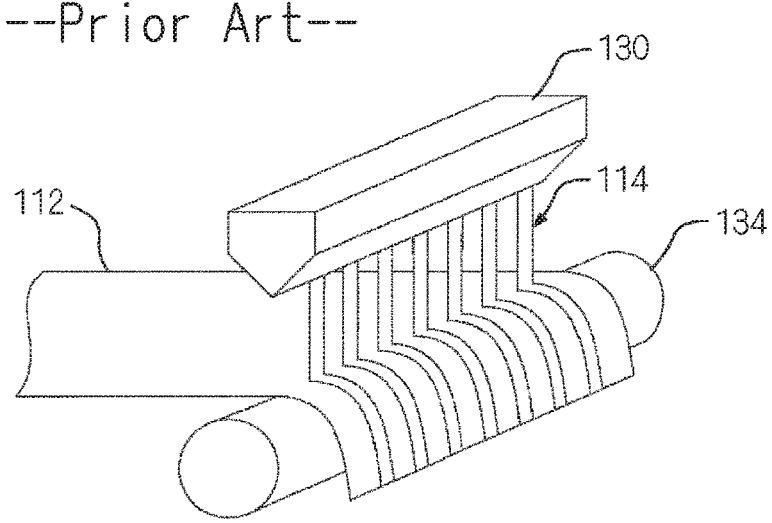

PRODUCTION METHOD OF ELASTIC COMPOSITE SHEET, ELASTIC COMPOSITE SHEET, AND DISPOSABLE WEARABLE ARTICLE USING SAID ELASTIC COMPOSITE SHEET

RELATED APPLICATIONS

The present application is National Phase of International Application No. PCT/JP2018/046425 filed Dec. 17, 2018, and claims a priority from Japanese Application No. 2018-014324, filed Jan. 31, 2018, the disclosure of which is hereby incorporated by reference herein in its entirety.

TECHNICAL FIELD

The present invention relates to elastic composite sheet production methods, elastic composite sheets, and disposable wearable articles including the elastic composite sheets. The present invention more particularly relates to an elastic composite sheet production method that involves, when an elastic member is brought out of a stretched state, causing a base material sheet to bend to make its surface uneven, an elastic composite sheet, and a disposable wearable article including the elastic composite sheet.

BACKGROUND ART

Elastic composite sheets, each including an elastic member and a base material sheet bonded to each other, are used for disposable wearable articles, such as disposable diapers.

FIG. 10 is a diagram schematically illustrating an elastic composite sheet production method. As illustrated in FIG. 10, the elastic composite sheet is manufacturable by extruding a molten or semi-molten elastic material 114 from a die 130 directly onto a nonwoven fabric web 112 in contact with a roller 134, and laminating and bonding a nonwoven fabric web (not illustrated) thereto (see, for example, Patent Literature 1).

CITATION LIST

Patent Literature

[Patent Literature 1] Japanese Translation of PCT International Application Publication No. JP-T-2015-529165

SUMMARY OF THE INVENTION

Problem to be Solved by the Invention

Laminating and bonding an elastic member (such as rubber threads) in a stretched state to a base material sheet (such as a nonwoven fabric) enables production of an elastic composite sheet whose base material sheet bends and makes its surface uneven when the elastic member is brought out of the stretched state.

The method illustrated in FIG. 10, however, involves bonding the elastic member to the nonwoven fabric immediately after the elastic member is extruded. The method thus fails to produce an elastic composite sheet whose surface is uneven.

To solve this problem, the inventor of this application came up with the idea of laminating and bonding an extruded elastic member in a stretched state to a base material sheet and carried out experiments on this idea. The inventor was then confronted with a new problem hitherto unknown, which is that ultrasonically bonding an elastic member in a stretched state to a base material sheet may result in breakage of the elastic member.

In view of these circumstances, a problem to be solved by the present invention is to provide an elastic composite sheet production method that is able to prevent breakage of an elastic member when the elastic member in a stretched state is bonded to a base material sheet, an elastic composite sheet, and a disposable wearable article including the elastic composite sheet.

Means for Solving the Problem

For the purpose of resolving the above-mentioned problem, the present invention provides an elastic composite sheet production method having features described below.

The elastic composite sheet production method includes: (i) a first step involving stretching a strip-shaped or string-shaped elastic member in a longitudinal direction of the elastic member, the elastic member being composed mainly of a thermoplastic elastic resin; (ii) a second step involving placing the stretched elastic member over a first base material sheet in a manner that a main surface of the first base material sheet comes into contact with the elastic member; and (iii) a third step involving, with the stretched elastic member placed over the first base material sheet, bonding the elastic member to the first base material sheet at a first location overlapping the elastic member and located away from edges of the elastic member as viewed in a direction perpendicular to the main surface of the first base material sheet.

The above method is able to prevent breakage of the elastic member when the elastic member in the stretched state is bonded to the base material sheet, because the first location (where the elastic member is to be bonded to the base material sheet) is located away from the edges of the elastic member.

Preferably, the elastic member is provided by extruding a heated and molten elastic resin material in a form of a strip. The elastic resin material is composed mainly of the thermoplastic elastic resin.

In this case, the elastic member is manufacturable more simply than when a strip-shaped elastic member is manufactured by cutting a sheet material.

Preferably, the second step involves placing a second base material sheet over the elastic member and the first base material sheet in a manner that the elastic member is sandwiched between the first base material sheet and the second base material sheet. The third step involves bonding the second base material sheet to at least either one of the elastic member and the first base material sheet.

In this case, the method enables production of the elastic composite sheet in which the elastic member is disposed between the first base material sheet and the second base material sheet.

Preferably, the first step involves disposing a plurality of the elastic members spaced from each other and stretching each of the elastic members in the longitudinal direction. The second step involves placing the stretched elastic members over the first base material sheet.

In this case, the method enables production of the elastic composite sheet in which the elastic members are disposed.

Preferably, the third step involves bonding the elastic member to the first base material sheet at intervals in a direction of extension of the elastic member.

In this case, the method enables production of the elastic composite sheet in which the elastic member is bonded to the first base material sheet at intervals.

Preferably, the third step involves bonding the first base material sheet to the second base material sheet at a second location located away from the elastic member as viewed in a direction perpendicular to the main surface of the first base material sheet.

In this case, the method enables production of the elastic composite sheet in which the first base material sheet is bonded to the second base material sheet.

Preferably, the third step involves bonding the first base material sheet to the second base material sheet at a third location adjacent to an associated one of the edges of the elastic member as viewed in a direction perpendicular to the main surface of the first base material sheet.

In this case, the method enables production of the elastic composite sheet in which the position of the elastic member brought out of the stretched state is restricted by a junction formed at the third location where the first and second base material sheets are bonded to each other.

Preferably, the third step involves bonding the first base material sheet to the second base material sheet at pairs of third locations. The third locations in each pair face each other and are each adjacent to an associated one of the edges of the elastic member as viewed in a direction perpendicular to the main surface of the first base material sheet.

In this case, the method enables production of the elastic composite sheet in which the position of the elastic member brought out of the stretched state is restricted by junctions formed at the third locations where the first and second base material sheets are bonded to each other.

Preferably, for bonding in the third step, ultrasonic bonding is used.

In this case, the method enables bonding at desired locations with greater ease and precision than when heat sealing, for example, is carried out.

To achieve the above object, the present invention provides an elastic composite sheet having features described below.

The elastic composite sheet includes: (a) a base material sheet; and (b) a strip-shaped or string-shaped elastic member composed mainly of a thermoplastic elastic resin and bonded to the base material sheet in a manner that the elastic member is in contact with a main surface of the base material sheet. With the elastic member stretched in a longitudinal direction of the elastic member, the elastic member is bonded, at intervals in a direction of extension of the elastic member, to the base material sheet at a plurality of locations overlapping the main surface of the elastic member and located away from edges of the elastic member as viewed in a direction perpendicular to the main surface of the base material sheet.

To achieve the above object, the present invention provides a disposable wearable article including the elastic composite sheet and having features described below.

The disposable wearable article includes: (a) a front waist portion; (b) a rear waist portion spaced from and facing the front waist portion; and (c) a crotch portion connected to the front waist portion and the rear waist portion. One or both of the front waist portion and the rear waist portion includes or include the elastic composite sheet. The elastic composite sheet is disposed in a manner that the elastic member extends in a direction around a waist of the disposable wearable article.

The disposable wearable article having the above features allows the front waist portion and the rear waist portion to have elasticity in a direction around the waist.

Effects of the Invention

The present invention makes it possible to prevent breakage of an elastic member when the elastic member in a stretched state is bonded to a base material sheet.

BRIEF DESCRIPTION OF DRAWINGS

FIG. 3(a) is a schematic cross-sectional view of a laminated body. FIG. 3(b) is a schematic transparent view of the laminated body (First Embodiment).

FIG. 9 is a schematic diagram of a disposable wearable article (Third Embodiment).

FIG. 10 is a diagram schematically illustrating an elastic composite sheet production method (Conventional Example 1).

MODE FOR CARRYING OUT THE INVENTION

Embodiments of the present invention will be described below with reference to the drawings.

First Embodiment

An elastic composite sheet production method and an elastic composite sheet according to first embodiment will be described with reference to FIG. 1 to FIG. 7(b).

Figure 1:
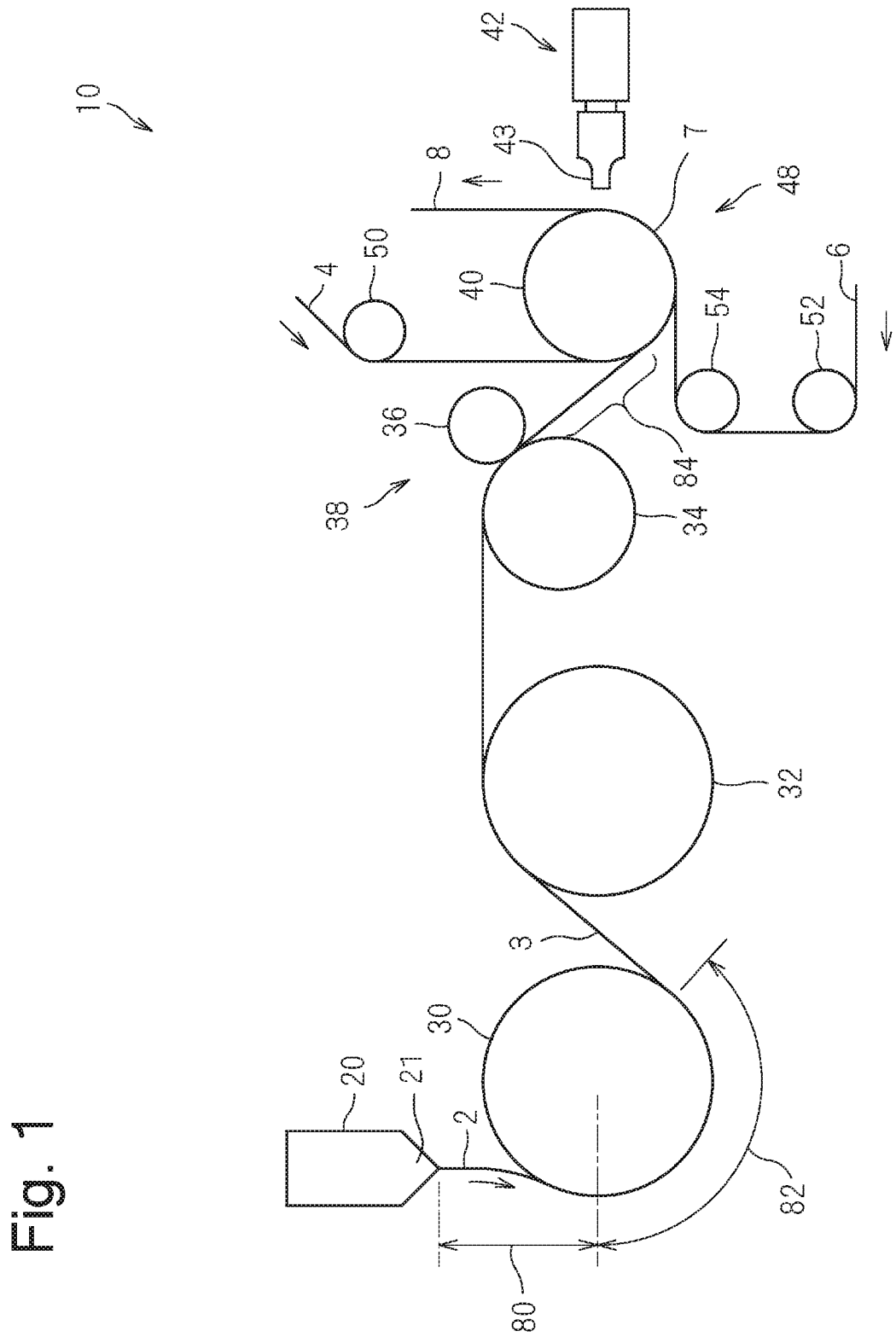
FIG. 1 is a schematic diagram illustrating an overall structure of an elastic composite sheet production apparatus (First Embodiment).

FIG. 1 is a schematic diagram illustrating an overall structure of an elastic composite sheet production apparatus 10. As illustrated in FIG. 1, the elastic composite sheet production apparatus 10 includes a discharger 20, a cooling roller 30, a stretcher 38, a laminator 48, and a controller (not illustrated). The controller exercises control such that the discharger 20, the cooling roller 30, the stretcher 38, and the laminator 48 operate in conjunction with each other.

The discharger 20 discharges a heated and molten elastic resin material in the form of a strip so as to form a strip-shaped intermediate 2. The elastic resin material is composed mainly of a thermoplastic elastic resin. The elastic resin material is heated to a temperature higher than a temperature range in which the elastic resin material elastically deforms, such that the elastic resin material melts. The discharger 20 may discharge a heated and molten elastic resin material in the form of a linear shape so as to form a string-shaped or line-shaped intermediate.

Figure 2A:
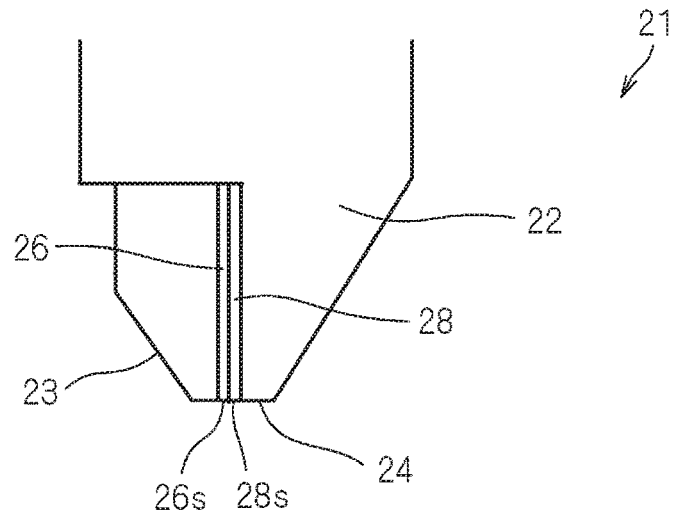
FIG. 2(a) is an enlarged schematic view of a discharge port assembly of a discharge.
Figure 2B:
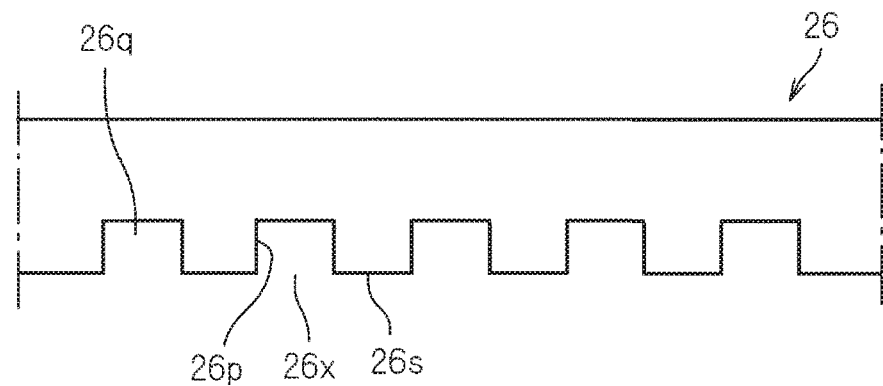
FIG. 2(b) is an enlarged schematic view of a first shim.
Figure 2C:
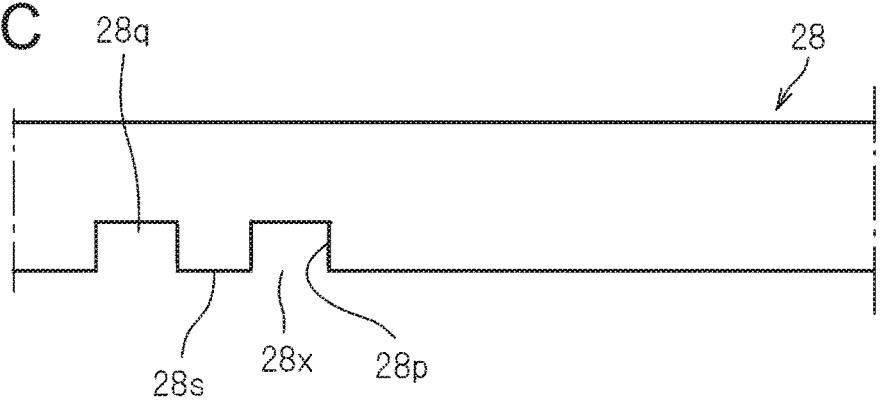
FIG. 2(c) is an enlarged schematic view of a second shim.
Figure 2D:
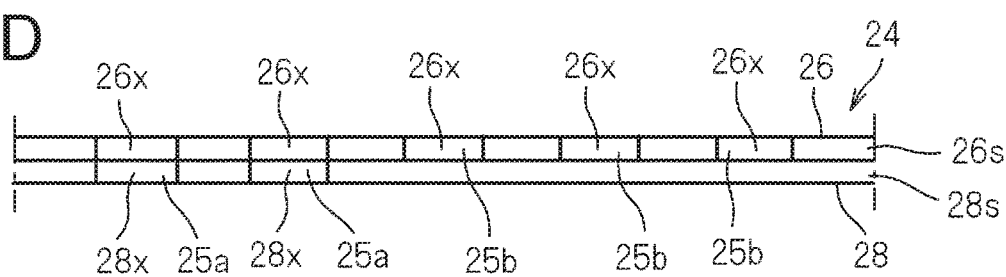
FIG. 2(d) is a schematic bottom view of the discharge port assembly of the discharger (First Embodiment).

FIG. 2(a) is an enlarged schematic view of a discharge port assembly 21 of the discharger 20. FIG. 2(b) is a schematic plan view of a first shim 26. FIG. 2(c) is a schematic plan view of a second shim 28. FIG. 2(d) is a schematic bottom view of the discharge port assembly 21 of the discharger 20.

As illustrated in FIG. 2(a), the first and second shims 26 and 28 each having a plate shape are secured to the lower portion of a discharge port assembly body 22 with a presser 23 and a fastener such as a bolt (not illustrated). The discharge port assembly body 22 and the presser 23 are provided with flow passages (not illustrated) through which the elastic resin material (which has been heated and molten) flows.

As illustrated in FIG. 2(b), the first shim 26 is provided with grooves 26p passing through the thickness direction of the first shim 26. As illustrated in FIG. 2(c), the second shim 28 is provided with grooves 28p passing through the thickness direction of the second shim 28. The grooves 26p are in communication with openings 26x defined in a lower surface 26s of the first shim 26. The grooves 28p are in communication with openings 28x defined in a lower surface 28s of the second shim 28. For example, the first shim 26 is provided with the grooves 26p across the width direction (which corresponds to the right-left direction in FIG. 2(b)). The second shim 28 is provided with the grooves 28p in the ends of the second shim 28 in the width direction (which corresponds to the right-left direction in FIG. 2(c)), with no groove 28p provided in an intermediate portion of the second shim 28 in the width direction.

The first and second shims 26 and 28 are secured to the discharge port assembly body 22, with the grooves 28p of the second shim 28 overlapping the grooves 26p of the first shim 26. Specifically, the first and second shims 26 and 28 are secured to the discharge port assembly body 22 such that the flow passages (not illustrated) in the presser 23 are in communication with upper portions 26q of the grooves 26p of the first shim 26 and upper portions 28q of the grooves 28p of the second shim 28 are in communication with the upper portions 26q of the grooves 26p of the first shim 26.

As illustrated in FIG. 2(d), a bottom surface 24 of the discharge port assembly body 22 is provided with: first discharge ports 25a including the openings 26x of the first shim 26 and the openings 28x of the second shim 28 adjacent to each other; and second discharge ports 25b consisting of the openings 26x of the first shim 26. The first discharge ports 25a are larger in width than the second discharge ports 25b. The elastic resin material, which has been heated and molten, is discharged from the first and second discharge ports 25a and 25b such that the elastic resin material discharged from the first discharge ports 25a differs in thickness from the elastic resin material discharged from the second discharge ports 25b.

As illustrated in FIG. 1, the cooling roller 30 is disposed below the discharger 20. The intermediate 2 discharged from the discharger 20 is drawn when necessary in a first section 80 defined between the discharger 20 and the cooling roller 30. The cooling roller 30 rotates at a peripheral speed higher than a feed speed at which the elastic resin material is discharged from the discharge ports of the discharger 20. The intermediate 2 is thus drawn until the thickness of the strip-shaped intermediate 2 reaches a predetermined value.

The cooling roller 30 is internally provided with a flow passage (not illustrated) through which a coolant flows. In a second section 82 where the intermediate 2 is in contact with the outer peripheral surface of the cooling roller 30, the coolant cools the intermediate 2 to a temperature range in which the elastic resin material (which constitutes the intermediate 2) elastically deforms, such that the intermediate 2 is solidified. This changes the intermediate 2 into a strip-shaped elastic member 3 in the second section 82. The elastic member 3 is then delivered out of the cooling roller 30.

The elastic member 3 is delivered to a guide roller 32 and then to the stretcher 38. The stretcher 38 includes a delivery roller 34, a pinch roller 36, and a stretching roller 40. The elastic member 3 is sandwiched between the delivery roller 34 and the pinch roller 36 such that the elastic member 3 does not slip on the outer peripheral surface of the delivery roller 34. Rotation of the delivery roller 34 synchronizes with rotation of the cooling roller 30.

The elastic member 3 is stretched in a third section 84 defined between an in-between space of the delivery roller 34 and the pinch roller 36 and the stretching roller 40. Specifically, the stretching roller 40 rotates at a peripheral speed higher than the peripheral speed of the delivery roller 34 so as to stretch the elastic member 3 by a predetermined factor. The elastic member 3 is thus stretched along the outer peripheral surface of the stretching roller 40.

The laminator 48 supplies a first nonwoven fabric 4 in a continuous form to a guide roller 50 and then to the stretching roller 40. The first nonwoven fabric 4 is a first base material sheet. The laminator 48 supplies a second nonwoven fabric 6 in a continuous form to guide rollers 52 and 54 and then to the stretching roller 40. The second nonwoven fabric 6 is a second base material sheet. The elastic member 3 stretched along the stretching roller 40 is sandwiched between the first nonwoven fabric 4 and the second nonwoven fabric 6. This provides a laminated body 7 in which the elastic member 3, the first nonwoven fabric 4, and the second nonwoven fabric 6 are laminated to each other.

The laminated body 7 moves in accordance with the rotation of the stretching roller 40 and passes through a space between the stretching roller 40 and a horn 43 of an ultrasonic bonder 42. The horn 43 moves close to and away from the stretching roller 40, such that the elastic member 3 is ultrasonically bonded to the first and second nonwoven fabrics 4 and 6 when the laminated body 7 is located between the stretching roller 40 and the horn 43. This provides an elastic composite sheet 8 in which the elastic member 3 is bonded at intervals to the first and second nonwoven fabrics 4 and 6. The elastic composite sheet 8 is then delivered out of the laminator 48. Portions of the first and second nonwoven fabrics 4 and 6 directly facing each other may be ultrasonically bonded to each other, with no elastic member 3 interposed therebetween.

Specifically, the stretching roller 40 is provided on its outer peripheral surface with protrusions (not illustrated) spaced from each other and thus functions as an anvil. A portion of the laminated body 7 located between the protrusions of the stretching roller 40 and the horn 43 is subjected to ultrasonic bonding. Such ultrasonic bonding enables the laminated body 7 to be subjected to bonding at desired locations with ease and precision.

In an example where a bonding method other than ultrasonic bonding is used, the elastic member 3 of the laminated body 7 may be bonded to the first and second nonwoven fabrics 4 and 6 by thermal welding, such as heat sealing. Alternatively, the elastic member 3 and the first and second nonwoven fabrics 4 and 6 may be provided with holes passing therethrough. The nonwoven fabrics 4 and 6 may be bonded to each other through these holes.

The stretching roller 40 serves not only as a roller included in the stretcher 38 but also as a roller included in the laminator 48. The elastic composite sheet production apparatus 10 is thus simplified in structure. Alternatively, the stretcher 38 and the laminator 48 may include different rollers.

Bonding patterns between the elastic member 3 and the first and second nonwoven fabrics 4 and 6 will be described below with reference to FIGS. 3, 4, and 7.

FIG. 3(a) is a schematic cross-sectional view of the laminated body 7. As illustrated in FIG. 3(a), the strip-shaped elastic member 3 is disposed between the first nonwoven fabric 4 and the second nonwoven fabric 6. The strip-shaped elastic member 3 includes: elongated main surfaces 3a and 3b facing each other; and elongated lateral surfaces 3s and 3t facing each other. The lateral surfaces 3s and 3t are smaller in width than the main surfaces 3a and 3b. The cross-sectional shape of the elastic member 3 is not limited to a rectangular shape. The elastic member 3 may be, for example, oval, elliptical, or circular in cross section.

FIG. 3(b) is a schematic transparent view of the laminated body 7 as viewed in a direction perpendicular to the main surface of the first nonwoven fabric 4. As illustrated in FIG. 3(b), the elastic member 3 is ultrasonically bonded at intervals to the first and second nonwoven fabrics 4 and 6 at first locations 60 such that junctions 60x are formed, and the first nonwoven fabric 4 is ultrasonically bonded at intervals to the second nonwoven fabric 6 at second locations 62 such that junctions 62x are formed. The first locations 60 overlap the elastic member 3 and are located away from edges 3p and 3q of the elastic member 3 as viewed in the direction perpendicular to the main surface of the first nonwoven fabric 4. The second locations 62 are located away from the elastic member 3 as viewed in the direction perpendicular to the main surface of the first nonwoven fabric 4.

A width W0 of the stretched elastic member 3 may be, for example, about 0.1 to 3 mm. A width W1 of each junction 60x at the first locations 60 is preferably ½ or less of the width W0 of the stretched elastic member 3 and is more preferably ⅓ or less of the width W0 of the stretched elastic member 3. A length L of each junction 60x is preferably about a few or several times as large as the width W1 of each junction 60x.

The elastic composite sheet illustrated in FIGS. 3(a) and 3(b) includes: FIG. 3(a) the nonwoven fabrics 4 and 6; and FIG. 3(b) the strip-shaped elastic member 3 composed mainly of a thermoplastic elastic resin and bonded to the nonwoven fabrics 4 and 6 such that the elastic member 3 is in contact with the main surfaces of the nonwoven fabrics 4 and 6. With the elastic member 3 stretched in the longitudinal direction of the elastic member 3, the elastic member 3 is bonded, at intervals in the direction of extension of the elastic member 3, to the nonwoven fabrics 4 and 6 at the locations 60 overlapping the elastic member 3 and located away from the edges 3p and 3q of the elastic member 3 as viewed in the direction perpendicular to the main surfaces of the nonwoven fabrics 4 and 6.

Figure 7A:
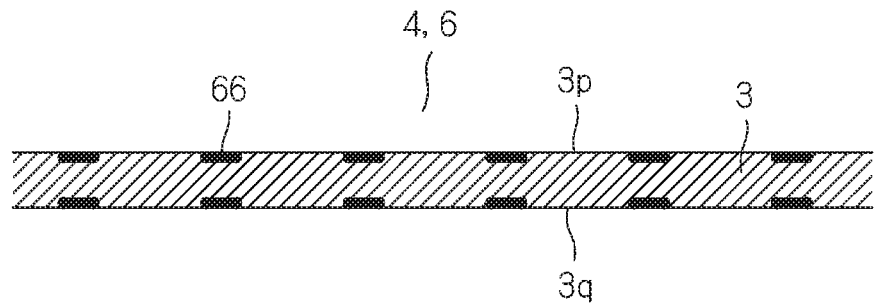
FIGS. 7(a) and 7(b) show schematic diagrams illustrating bonding patterns between an elastic member and first and second nonwoven fabrics (Comparative Examples 1 and 2).
Figure 7B:
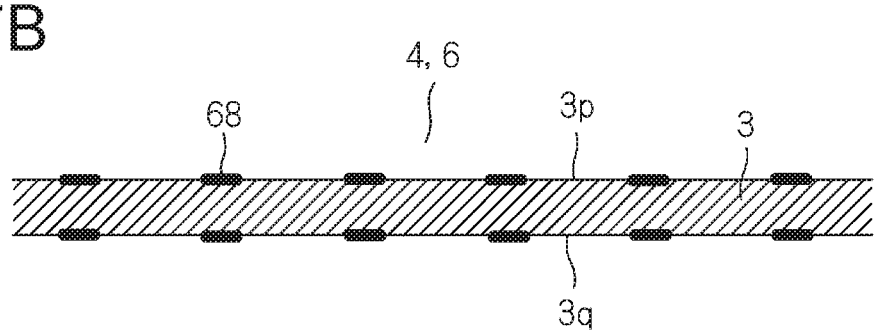

FIGS. 7(a) and 7(b) show schematic diagrams illustrating, similarly to FIG. 3(b), bonding patterns between the elastic member 3 and the first and second nonwoven fabrics 4 and 6 according to Comparative Examples 1 and 2. The inventor of this application was confronted with a new problem hitherto unknown, which is that the elastic member 3 may break when the elastic member 3 is ultrasonically bonded to the first and second nonwoven fabrics 4 and 6 at locations 66 in contact with the edges 3p and 3q of the stretched elastic member 3 as illustrated in FIG. 7(a), or when the elastic member 3 is ultrasonically bonded to the first and second nonwoven fabrics 4 and 6 at locations 68 overlapping the edges 3p and 3q of the stretched elastic member 3 as illustrated in FIG. 7(b).

A solution to this problem involves, as illustrated in FIG. 3(b), ultrasonically bonding the elastic member 3 to the first and second nonwoven fabrics 4 and 6 at the first locations 60 located away from the edges 3p and 3q of the elastic member 3. This makes it possible to prevent breakage of the elastic member 3.

Figure 4A:
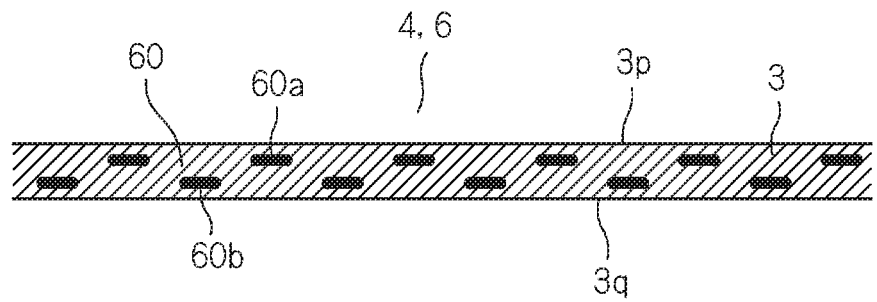
FIGS. 4(a) and 4(b) show schematic diagrams illustrating bonding patterns between an elastic member and first and second nonwoven fabrics (Variations 1 and 2).
Figure 4B:
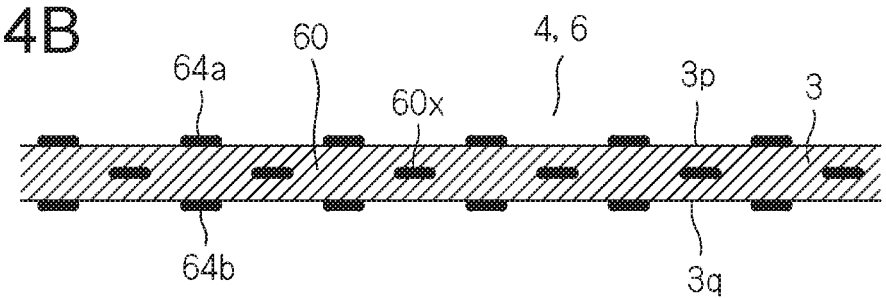

FIGS. 4(a) and 4(b) show schematic diagrams illustrating, similarly to FIG. 3(b), variations of bonding patterns between the elastic member 3 and the first and second nonwoven fabrics 4 and 6.

As illustrated in FIG. 4(a), one variation may involve bonding the elastic member 3 to the first and second nonwoven fabrics 4 and 6 at the first locations 60 such that junctions 60a and 60b are formed at positions away from the center of the elastic member 3.

As illustrated in FIG. 4(b), another variation may involve, in addition to bonding the elastic member 3 to the first and second nonwoven fabrics 4 and 6 at the first locations 60, bonding the first nonwoven fabric 4 to the second nonwoven fabric 6 at pairs of third locations 64a and 64b. The third locations 64a and 64b in each pair face each other and are each adjacent to an associated one of the edges 3p and 3q of the elastic member 3 as viewed in the direction perpendicular to the main surface of the first nonwoven fabric 4. The first nonwoven fabric 4 may be bonded to the second nonwoven fabric 6 at either the locations 64a or the locations 64 included in the pairs of third locations 64a and 64b adjacent to the edges 3p and 3q of the elastic member 3. The third locations 64a and 64b where the first nonwoven fabric 4 is to be bonded to the second nonwoven fabric 6 (i.e., the locations 64a adjacent to the edge 3p of the elastic member 3 and the locations 64b adjacent to the edge 3q of the elastic member 3) may be deviated from each other in the direction of extension of the elastic member 3.

Any of these variations enables production of an elastic composite sheet in which the position of the elastic member 3 brought out of a stretched state is restricted by junctions formed at the third locations 64a and 64b where the first nonwoven fabric 4 is bonded to the second nonwoven fabric 6.

Figure 5A:
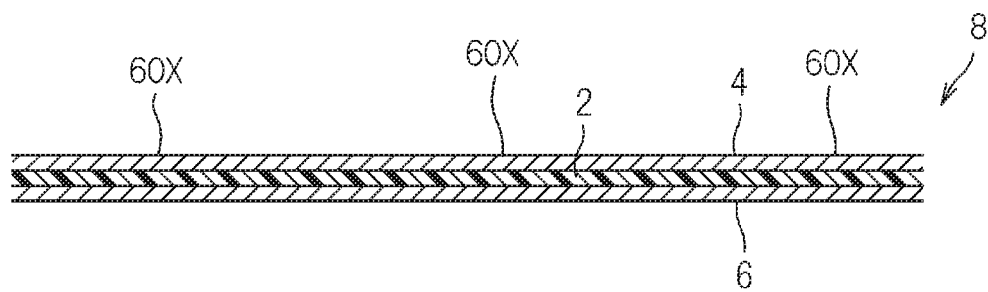
FIG. 5(a) is a cross-sectional view of an elastic composite sheet when the elastic member is in a stretched state.
Figure 5B:
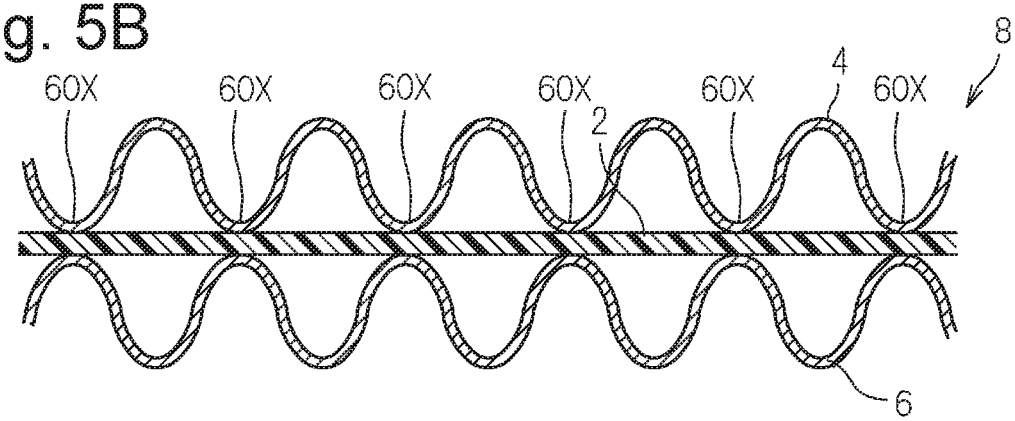
FIG. 5(b) is a cross-sectional view of the elastic composite sheet when the elastic member is brought out of the stretched state (First Embodiment).

FIG. 5(a) is a cross-sectional view of the elastic composite sheet 8 when the elastic member 3 is in a stretched state. FIG. 5(b) is a cross-sectional view of the elastic composite sheet when the elastic member 3 is brought out of the stretched state. Suppose that as illustrated in FIG. 5(a), the elastic member 3 is bonded at intervals to the first and second nonwoven fabrics 4 and 6 at the first locations such that the junctions 60x are formed. In this case, as illustrated in FIG. 5(b), bringing the elastic member 3 out of the stretched state reduces the spaces between the junctions 60x adjacent to each other and bends the first and second nonwoven fabrics 4 and 6, making the surfaces of the first and second nonwoven fabrics 4 and 6 uneven.

Figure 6A:
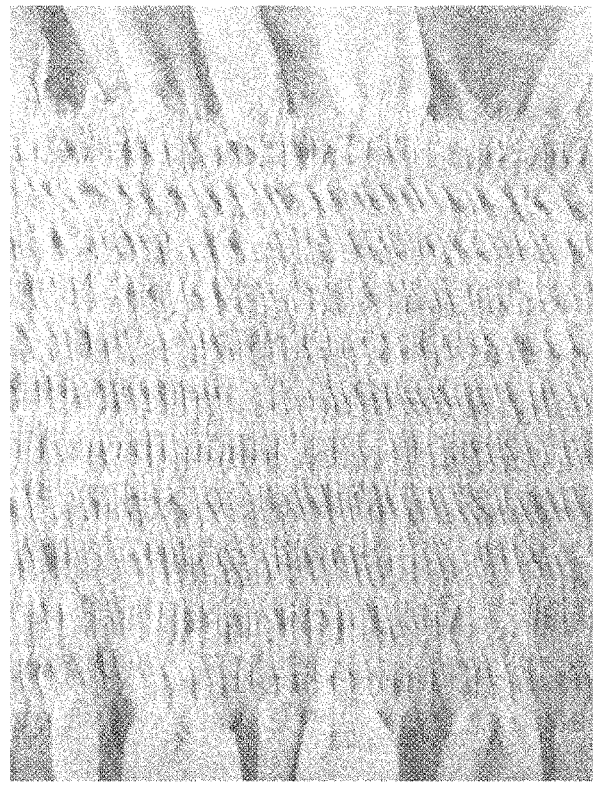
FIGS. 6(a) and 6(b) show photographs illustrating an example of fabricating the elastic composite sheet (First Embodiment).
Figure 6B:
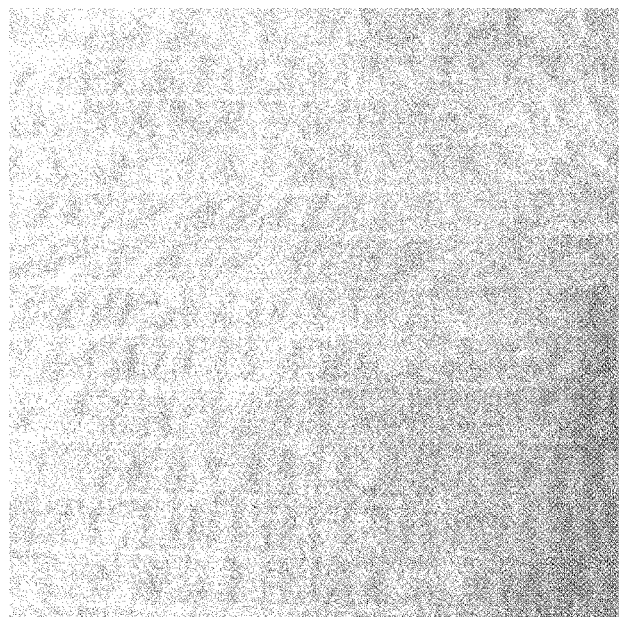

FIGS. 6(a) and 6(b) show photographs illustrating an example of fabricating an elastic composite sheet. FIG. 6(a) illustrates a natural state where corrugated unevenness is developed on the surface of the elastic composite sheet. FIG.

6(b) illustrates the elastic composite sheet in a stretched state. FIG. 6(b) suggests that elastic members are stretched in the right-left direction such that the corrugated unevenness on the surfaces of nonwoven fabrics is removed, and the nonwoven fabrics are bonded to each other sporadically in regions where the nonwoven fabrics do not overlap the elastic members.

A thermoplastic elastic resin to be used as a material for the elastic member 3 is preferably a thermoplastic resin that exhibits rubber elasticity at room temperature. One example may involve selecting a suitable type of thermoplastic resin from thermoplastic elastomers specified and classified in JIS K 6418: 2007 (ISO 18064: 2003). Another example may involve using a thermoplastic elastomer whose hard segment has a glass transition temperature of about 80° C. to about 200° C. and whose soft segment has a glass transition temperature of −70° C. to −10° C.

Specific examples of such elastomers may include an olefinic elastomer, such as "VERSIFY" (registered trademark) produced by the Dow Chemical Company, a propylene elastomer, such as "Vistamaxx" (registered trademark) produced by Exxon Mobil Corporation, and a styrene elastomer, such as "Quintac" (registered trademark) produced by Zeon Corporation.

An elastic composite sheet production method according to first embodiment will be described below with reference to FIGS. 3(a) and 3(b). First, the method includes a first step involving stretching the strip-shaped or string-shaped elastic member 3, which is composed mainly of a thermoplastic elastic resin, in the longitudinal direction of the elastic member 3.

The method then includes a second step involving placing the stretched elastic member 3 over the first nonwoven fabric 4 such that the main surface of the first nonwoven fabric 4 comes into contact with the elastic member 3. The second step includes a first sub-step involving placing the second nonwoven fabric 6 over the elastic member 3 and the first nonwoven fabric 4 such that the elastic member 3 is sandwiched between the first nonwoven fabric 4 and the second nonwoven fabric 6.

The method then includes a third step involving, with the stretched elastic member 3 placed over the first nonwoven fabric 4, bonding the elastic member 3 to the first nonwoven fabric 4 at the first locations 60 overlapping the elastic member 3 and located away from the edges 3p and 3q of the elastic member 3 as viewed in the direction perpendicular to the main surface of the first nonwoven fabric 4. The third step includes a second sub-step involving bonding the second nonwoven fabric 6 to at least either one of the elastic member 3 and the first nonwoven fabric 4.

The above method is able to prevent breakage of the elastic member 3 when the elastic member 3 is bonded to the first nonwoven fabric 4, because the first locations 60 (where the elastic member 3 is to be bonded to the first nonwoven fabric 4) are located away from the edges 3p and 3q of the elastic member 3.

Alternatively, the elastic member 3 may be bonded to the first nonwoven fabric 4 continuously in the direction of extension of the elastic member 3 instead of being bonded, at the first locations 60, to the first nonwoven fabric 4 at intervals in the direction of extension of the elastic member 3.

The third step may involve bonding the first and second nonwoven fabrics 4 and 6 to each other at the second locations 62 located away from the elastic member 3 as viewed in the direction perpendicular to the main surface of the first nonwoven fabric 4. In this case, the method is able to produce the elastic composite sheet in which the first and second nonwoven fabrics 4 and 6 are bonded to each other. The method, however, may skip bonding at the second locations 62.

The elastic composite sheet production apparatus 10 may be configured such that the discharger 20 discharges a plurality of the intermediates 2 so as to form a plurality of the elastic members 3, the elastic members 3 are spaced from each other and stretched in the longitudinal direction of the elastic members 3 in the third section 84, and the laminator 48 laminates the stretched elastic members 3 to the first and second nonwoven fabrics 4 and 6. This enables production of the elastic composite sheet 8 in which the elastic members 3 are disposed.

The method may involve extruding a heated and molten elastic resin material in the form of a strip. Thus, an elastic member is manufacturable more simply than when a strip-shaped elastic member is manufactured by cutting a sheet material.

The method may involve, instead of extruding an elastic member using the elastic composite sheet production apparatus, preparing, for example, a pre-processed elastic member in a rolled form and unrolling the prepared elastic member in producing an elastic composite sheet.

Variation 1

The laminator 48 of the elastic composite sheet production apparatus 10 may be configured to supply the first nonwoven fabric 4 instead of supplying both of the first and second nonwoven fabrics 4 and 6 and to laminate and bond the elastic member 3 to the first nonwoven fabric 4. Also in this case, breakage of the elastic member 3 is preventable when the elastic member 3 in a stretched state is bonded to the first nonwoven fabric 4.

The second step of the elastic composite sheet production method according to Variation 1 does not include the first sub-step included in the elastic composite sheet production method according to first embodiment described above. The third step of the elastic composite sheet production method according to Variation 1 does not include the second sub-step.

Second Embodiment

Figure 8:
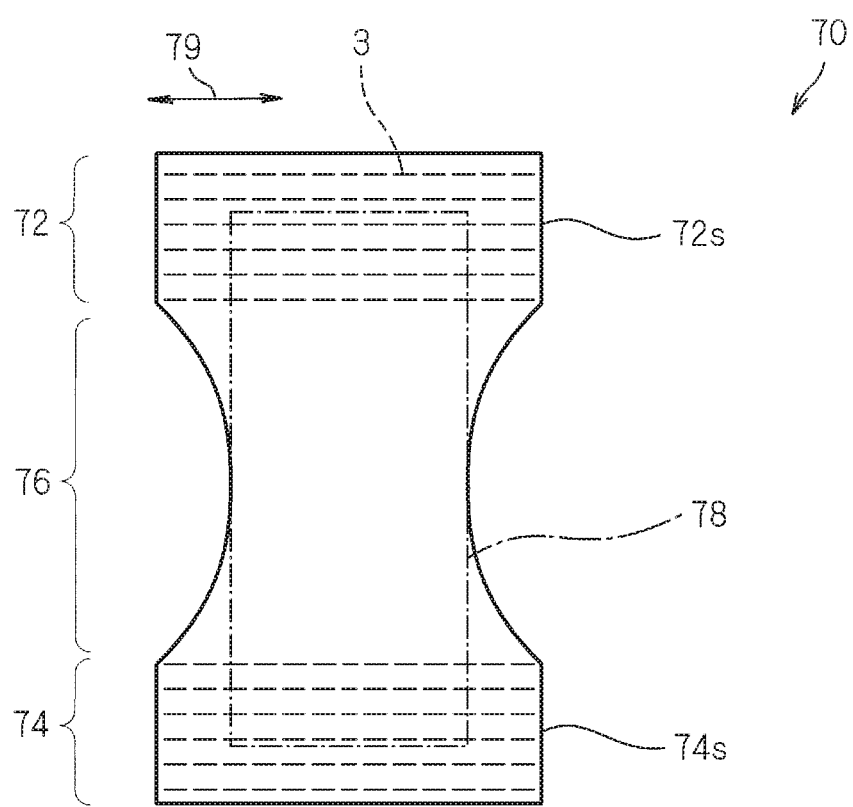
FIG. 8 is a schematic diagram of a disposable wearable article (Second Embodiment).

A disposable wearable article 70 including the elastic composite sheet 8 produced in first embodiment will be described with reference to FIG. 8. FIG. 8 is a schematic diagram of the disposable wearable article 70.

As illustrated in FIG. 8, the disposable wearable article 70 includes a front waist portion 72, a rear waist portion 74, and a crotch portion 76. The front waist portion 72 and the rear waist portion 74 are spaced from each other and face each other. The crotch portion 76 is connected to the front waist portion 72 and the rear waist portion 74. An absorber 78 indicated by the chain line is disposed such that the absorber 78 straddles the crotch portion 76. During use, the disposable wearable article 70 is bent at the crotch portion 76 such that the front waist portion 72 is located on or adjacent to the stomach and the rear waist portion 74 is located on or adjacent to the back, and the front waist portion 72 and the rear waist portion 74 are fastened to each other with a fastener, such as a tape (not illustrated).

When the disposable wearable article is of an "underwear type", a pair of sides 72s of the front waist portion 72 and a pair of sides 74s of the rear waist portion 74 are bonded to each other in advance by, for example, heat sealing.

The elastic composite sheet 8 according to first embodiment is used for the front waist portion 72 and the rear waist portion 74 of the disposable wearable article 70. The elastic composite sheet 8 is disposed such that the elastic members 3 indicated by the broken lines extend in a direction around the waist of the disposable wearable article shown by a double-headed arrow 79. The disposable wearable article 70 thus allows the front waist portion 72 and the rear waist portion 74 to have elasticity in the direction around the waist. The use of the elastic composite sheet 8 according to first embodiment easily allows the elastic members 3 to have desired properties, such as desired stretching stress and stretching rate, in accordance with regions where the elastic members 3 are to be used.

The elastic composite sheet 8 according to first embodiment may be used for the front waist portion 72 and the rear waist portion 74 of the disposable wearable article 70 or may be used for the front waist portion 72, the rear waist portion 74, and the crotch portion 76 such that the elastic members 3 of the elastic composite sheet 8 are disposed to extend in a direction around the waist along either one of the front waist portion 72 and the rear waist portion 74. The elastic composite sheet 8 according to first embodiment may be used for either one of the front waist portion 72 and the rear waist portion 74 of the disposable wearable article 70 such that the elastic members 3 of the elastic composite sheet 8 are disposed to extend in a direction around the waist.

Third Embodiment

A disposable wearable article 70a including the elastic composite sheet 8 according to first embodiment, which is used for a pair of side panels 75, will be described with reference to FIG. 9. FIG. 9 is a schematic diagram of the disposable wearable article 70a in a spread state.

As illustrated in FIG. 9, the disposable wearable article 70a includes a body 71 whose first end 71b has the pair of side panels 75 bonded thereto and whose second end 71f has a pair of lugs 73 bonded thereto. A rear waist portion 74a includes the first end 71b of the body 71 and the pair of side panels 75. A front waist portion 72a includes the second end 71f of the body 71 and the pair of lugs 73. An absorber 78a is disposed on the body 71 such that the absorber 78a straddles a crotch portion 76a.

During use, the disposable wearable article 70a is bent at the crotch portion 76a such that the front waist portion 72a is located on or adjacent to the stomach and the rear waist portion 74a is located on or adjacent to the back, and first hook-and-loop fasteners 70s (which are provided on ends 75a of the side panels 75) are fastened to a second hook-and-loop fastener 70t (which is provided on the second end 71f of the body 71) such that the front waist portion 72a and the rear waist portion 74a are fastened to each other. The disposable wearable article 70a is thus worn by a user. The side panels 75 may be fastened to the second end 71f of the body 71 with, for example, tapes instead of the hook-and-loop fasteners 70s and 70t. The disposable wearable article 70a may be configured such that the front waist portion 72a includes the pair of side panels 75 and the rear waist portion 74a includes the pair of lugs 73.

The side panels 75 of the rear waist portion 74a include the elastic composite sheet 8 according to first embodiment. As indicated by the broken lines, the elastic members 3 of the elastic composite sheet 8 are disposed such that the elastic members 3 extend in a direction around the waist of the disposable wearable article 70a shown by the double-headed arrow 79.

The use of the elastic composite sheet 8 according to first embodiment easily allows the elastic members 3 to have desired properties, such as desired stretching stress and stretching rate, in accordance with the side panels 75.

SUMMARY

As described above, an elastic member is prevented from being broken when the elastic member in a stretched state is bonded to a base material sheet.

The present invention is not limited to the foregoing embodiments but may be practiced, with various modifications made thereto.

Although an elastic composite sheet in which an elastic member is laminated and bonded to a nonwoven fabric has been illustrated by way of example, an elastic composite sheet may be produced using a base material sheet other than a nonwoven fabric. The cross-sectional shape of an elastic member is not limited to a rectangular shape. An elastic member may be, for example, oval, elliptical, or circular in cross section.

REFERENCE SIGNS LIST 3 elastic member
3a, 3b main surface
3p, 3q edge
3s, 3t lateral surface
4 first nonwoven fabric (first base material sheet)
6 second nonwoven fabric (second base material sheet)
60 first location
62 second location
64a, 64b third location
70, 70a disposable wearable article
72, 72a front waist portion
74, 74a rear waist portion
76, 76a crotch portion
79 direction around waist

The invention claimed is:

1. A method for producing an elastic composite sheet, comprising:
   a first step of stretching a strip-shaped or string-shaped elastic member in a longitudinal direction of the elastic member, the elastic member comprising a thermoplastic elastic resin;
   a second step of placing the stretched elastic member over a first base material sheet in a manner that a main surface of the first base material sheet comes into contact with the elastic member; and
   a third step of, with the stretched elastic member placed over the first base material sheet, bonding the elastic member to a first location of the first base material sheet, the first location overlapping the elastic member and located away from edges of the elastic member as viewed in a direction perpendicular to the main surface of the first base material sheet, wherein
   the first step further comprises disposing a plurality of the elastic members spaced from each other and stretching each said elastic member of the plurality of elastic members in the longitudinal direction, and
   in the third step the stretched elastic members are placed over the first base material sheet, bonding the stretched elastic members to the first base material sheet at the first location overlapping the stretched elastic members in a manner so the edges of the stretched elastic members are not bonded to the first base material sheet, and the bonding is ultrasonic bonding.

2. The method for producing the elastic composite sheet according to claim 1, wherein the elastic member is provided by extruding a heated and molten elastic resin material in a form of a strip, the elastic resin material being composed mainly of the thermoplastic elastic resin.

3. The method for producing the elastic composite sheet according to claim 2, wherein
the second step involves placing a second base material sheet over the elastic member and the first base material sheet in a manner that the elastic member is sandwiched between the first base material sheet and the second base material sheet, and
the third step involves bonding the second base material sheet to at least either one of the elastic member and the first base material sheet.

4. The method for producing the elastic composite sheet according to claim 3, wherein
the third step involves bonding the first base material sheet to a second location of the second base material sheet, the second location located away from the elastic member as viewed in a direction perpendicular to the main surface of the first base material sheet.

5. The method for producing the elastic composite sheet according to claim 3, wherein
the third step involves bonding the first base material sheet to a third location of the second base material sheet, the third location adjacent to an associated one of the edges of the elastic member as viewed in a direction perpendicular to the main surface of the first base material sheet.

6. The method for producing the elastic composite sheet according to claim 3, wherein
the third step involves bonding the first base material sheet to the second base material sheet at pairs of third locations, the third locations in each pair facing each other and each being adjacent to an associated one of the edges of the elastic member as viewed in a direction perpendicular to the main surface of the first base material sheet.

7. The method for producing the elastic composite sheet according to claim 2, wherein
the third step involves bonding the elastic member to the first base material sheet at intervals in a direction of extension of the elastic member.

8. The method for producing the elastic composite sheet according to claim 1, wherein
the second step involves placing a second base material sheet over the elastic member and the first base material sheet in a manner that the elastic member is sandwiched between the first base material sheet and the second base material sheet, and
the third step involves bonding the second base material sheet to at least either one of the elastic member and the first base material sheet.

9. The method for producing the elastic composite sheet according to claim 8, wherein
the third step involves bonding the first base material sheet to a second location of the second base material sheet, the second location located away from the elastic member as viewed in a direction perpendicular to the main surface of the first base material sheet.

10. The method for producing the elastic composite sheet according to claim 9, wherein
the third step involves bonding the first base material sheet to a third location of the second base material sheet, the third location adjacent to an associated one of the edges of the elastic member as viewed in a direction perpendicular to the main surface of the first base material sheet.

11. The method for producing the elastic composite sheet according to claim 9, wherein
the third step involves bonding the first base material sheet to the second base material sheet at pairs of third locations, the third locations in each pair facing each other and each being adjacent to an associated one of the edges of the elastic member as viewed in a direction perpendicular to the main surface of the first base material sheet.

12. The method for producing the elastic composite sheet according to claim 8, wherein
the third step involves bonding the first base material sheet to a third location of the second base material sheet, the third location adjacent to an associated one of the edges of the elastic member as viewed in a direction perpendicular to the main surface of the first base material sheet.

13. The method for producing the elastic composite sheet according to claim 8, wherein
the third step involves bonding the first base material sheet to the second base material sheet at pairs of third locations, the third locations in each pair facing each other and each being adjacent to an associated one of the edges of the elastic member as viewed in a direction perpendicular to the main surface of the first base material sheet.

14. The method for producing the elastic composite sheet according to claim 1, wherein
the third step involves bonding the elastic member to the first base material sheet at intervals in a direction of extension of the elastic member.

* * * * *